United States Patent [19]

Jensen et al.

[11] Patent Number: 5,064,675

[45] Date of Patent: Nov. 12, 1991

[54] HERBAL EXTRACT COMPOSITION

[75] Inventors: Eigil Jensen, Järna; N. Urban Olsson, Kista; Peter Kaufmann, Järna; Anders Hagman, Sollentuna, all of Sweden

[73] Assignee: Scandinavian Natural Resources Development HB, Jarna, Sweden

[21] Appl. No.: 662,756

[22] Filed: Mar. 1, 1991

[51] Int. Cl.$^5$ .............................................. A23F 3/34
[52] U.S. Cl. ................................ 426/597; 426/424; 426/429; 426/489; 426/655; 426/638; 424/195.1
[58] Field of Search .............. 426/592, 597, 638, 655, 426/435, 429, 489, 424; 424/195.1

[56] References Cited

U.S. PATENT DOCUMENTS

| | | | |
|---|---|---|---|
| 685,853 | 11/1901 | Joie | 426/597 |
| 2,554,873 | 5/1951 | Musher | 426/655 |
| 2,636,888 | 4/1953 | Washburn | 426/655 |
| 2,971,844 | 2/1961 | Bosanac | 426/597 |
| 3,030,271 | 4/1962 | Lafon | 424/195.1 |
| 3,060,033 | 10/1962 | Ermarkaryan | 426/638 |
| 3,709,694 | 1/1973 | Killenyer | 426/435 |
| 3,809,769 | 5/1974 | Rivkowich | 426/655 |
| 3,873,752 | 3/1975 | Reymond | 426/655 |
| 4,450,097 | 5/1984 | Nakatani | 426/655 |
| 4,671,959 | 6/1987 | Warren | 424/195.1 |
| 4,683,140 | 1/1987 | Kang | 426/597 |
| 4,786,498 | 11/1988 | Isaac | 426/429 |
| 4,886,665 | 12/1989 | Kovacs | 424/195.1 |

FOREIGN PATENT DOCUMENTS

| | | | |
|---|---|---|---|
| 52-31039 | 12/1977 | Japan | 426/597 |
| 60-34138 | 2/1985 | Japan | 426/638 |
| 1-191680 | 8/1989 | Japan | 426/435 |
| 587151 | 1/1978 | U.S.S.R. | 426/592 |
| 699012 | 11/1979 | U.S.S.R. | 426/592 |
| 706441 | 12/1979 | U.S.S.R. | 426/592 |
| 797642 | 1/1981 | U.S.S.R. | 426/597 |
| 815030 | 3/1981 | U.S.S.R. | 426/592 |

*Primary Examiner*—Carolyn Paden
*Attorney, Agent, or Firm*—George A. Skoler

[57] ABSTRACT

Herbal Extract Composition containing a Melissa species extract, an Avena species extract and a Tilia species extract; a Modified Herbal Extract Composition containing additional herbal extracts; a Beverage Concentrate containing the Modified Herbal Extract Composition; amd a beverage made from the Beverage Concentrate dissolved/dispersed in water.

34 Claims, No Drawings

HERBAL EXTRACT COMPOSITION

BRIEF DESCRIPTION OF THE INVENTION

A herbal extract composition comprising a Melissa species extract, an Avena species extract and a Tilia species extract. The composition can further comprise at least one additional extract of a plant such as Citrus species, Crataegus species, Panax species, and Lavendula species. The herbal extract composition is useful in numerous forms including an extract concentrate for food and beverage preparation, additive or enhancer for existing foods and beverages and particularly in the form of a pleasant tasting and soothing beverage.

BACKGROUND TO THE INVENTION

Herbs and spices have long been used in food and beverage preparations. They have been used to enhance flavoring and provide for the user's overall sense of well-being. For example, Panax ginseng (*Asiatic ginseng*) provides root-derived preparations that are reported to variously stimulate and relax the nerves (see U.S. Pat. No. 4,446,130 discussed below). Typical dosages recommended for the elderly or for long-term disabilities are 400–800 mg. of dried root equivalent per day. Authorities on the subject recommend for stressful situations, in the young, 600–2,000 mg. of dried root equivalent per day for up to three weeks in any month.

Linden or limeflowers (*Tilia europaea*) provides flower-derived preparations that are reported to provide a relaxant and healing effect on blood vessel walls. They have been suggested for persons with cardivascular conditions who exhibit pronounced anxiety or tension factor. Dosages of 1–4 g. dried flowers equivalent, three or more times daily have been recommended. Teas prepared from Tilia are recognized as traditional domestic favorites.

Oats (*Avena sativa*) as whole plant preparations are widely recommended as being generally beneficial for all states of debility, particularly involving the nervous system (see U.S. Pat. No. 4,886,665 discussed below). They have been recommended to be taken for conditions such as depression, and a diverse spectrum of physical deseases. Recommended amounts are 1–4 g. dried herb or oatmeal equivalent three times daily.

Balm mint (*Melissa officinalis*) is known for its pleasant and characteristic scent. Whole plant preparations are recommended as relaxants for calming the nerves and for improving digestion. It is prepared as a drink to relieve a range of dyspeptic conditions. Recommended amounts are 1–4 g. dried herb equivalent at least three times daily.

Lavender (*Lavendula officinalis* and other L. species) is recommended for the same type applications as Balm mint. Recommended amounts are 0.5–2 g. dried flowers equivalent three times daily.

Several patents have issued that relate to various uses of herbs and herbal compositions, including the following. Grollier, et al., U.S. Pat. No. 4,767,618, describe cosmetic compositions that use both Melissa and Tilia. Hachiya et al., U.S. Pat. No. 4,446,130, describe a method of preparing dried ginseng and an alcoholic (ethanolic) beverage or elixir and reports that ginseng exhibits sedative, stimulative and diuretic activities.

Kovacs, U.S. Pat. No. 4,886,665, describes a food supplement composition containing an oat extract and an extract of nettle. The combined extracts can be in the form of powder added to a beverage or fruit juice to provide a nutritional drink. The powder products can be incorporated into other forms.

THE INVENTION

This invention relates to a Herbal Extract Composition that comprises a Melissa species extract, an Avena species extract and a Tilia species extract. Desirably, the Herbal Extract Composition comprises about 25 to about 75 volume percent of Melissa species extract, about 15 to about 50 volume percent of Avena species extract and about 3 to about 25 volume percent of a Tilia species extract. Preferably, the Herbal Extract Composition comprises about 30 to 65 volume percent of the Melissa species extract, about 20 to about 40 of the Avena species extract and about 5 to about 20 volume percent of the Tilia species extract. As with herbal compositions generally, the Herbal Extract Composition of the invention may be beneficially used to provide flavoring and contribute to a user's overall sense of well-being.

The invention also relates to a Modified Herbal Extract Composition that includes the Herbal Extract Composition and one or more of other extracts. These additional extracts include those from Citrus, Crataegus, Panax and Lavendula species. The Modified Herbal Extract Composition may take a number of forms such as an extract concentrate that is useful in food and beverage preparations, as an additive or enhancer for solid and liquid foods and beverages. When prepared in water and carbonated water, a Modified Herbal Extract Composition alone can be used to create a pleasant tasting and soothing beverage.

The Modified Herbal Extract Composition may yield the benefits of the Herbal Extract Composition of the invention, even when the final concentration of the Herbal Extract Composition is substantially lowered by dilution through the modification. Even when such modification enhances taste, making taste more pleasant and appealing, the benefits realized from foods and beverages, that are made of or contain the Herbal Extract Composition, can include (a) a soothing or calming effect and (b) restoration of energy and activity. Where Crataegus species, e.g. *Crataegus oxyacanta*, is included in a beverage containing the Herbal Extract Composition, long term restorative effects and enhancement of endurance are realized. Addition of lemon extract to the Herbal Extract Composition enhances the pleasant taste of foods and beverages that include or are preparations of the Modified Herbal Extract Composition or the Herbal Extract Composition.

Although the beneficial properties realized are a result of the combination of certain essential components of the Herbal Extract Composition, the primary effectors of certain of these properties, even when enhanced by modification by inclusion of other constituents, can be identified. For example, the soothing or calming effect is primarily associated with the presence of balm (*Melissa officinalis*) and oat (*Avena sativa*). The restoration of energy and activity is primarily associated with the balm constituent.

One embodiment of the invention is a beverage comprising a Modified Herbal Extract Composition specifically made as a Beverage Concentrate that is dispersed/dissolved in an aqueous carrier. The beverage may comprise about 1 to about 50 volume percent of Modified Herbal Extract Composition specifically developed for use as a Beverage Concentrate. Such a Beverage Concentrate is formulated for the express purpose of providing the benefits of the Herbal Extract Composition. A more desirable beverage composition comprises about 2 to about 45 volume percent of the Modified Herbal Extract Composition in the form of the Beverage Concentrate, preferably about 5 to about 40 volume percent of the Modified Herbal Extract Composition (in the form of the Beverage Concentrate), more preferably about 8 to about 35 volume percent of the Modified Herbal Extract composition (in the form of the Beverage Concentrate). A most preferred beverage composition contains about 10 to about 30 volume percent of the Modified Herbal Extract Composition (in the form of the Beverage Concentrate).

Another aspect of the invention is a process for preparing the herbal extract composition. The process includes the steps of:

(a) extracting dried leaves of a Melissa species with heat in a non-toxic extraction solvent such as aqueous ethanol and recovering by filtration the organic residue extract thereof;

(b) extracting an Avena species in powder form in a non-toxic extraction solvent such as aqueous ethanol and recovering by filtration the organic residue extract thereof;

(c) extracting in an ethanol solution the dried flowers of a Tilia species and recovering by filtration the organic residue extract thereof; and (d) combining the Melissa, Avena and Tilia extracts so recovered in the desired proportions.

DETAILED DESCRIPTION OF THE INVENTION

The Modified Herbal Extract Composition, as noted above, further comprises at least one additional plant extract, such as from Citrus species, Crataegus species, Panax species, and Lavendula species. For example, the Modified Herbal Extract Composition may comprise about 40 to about 70 volume percent of a citrus extract and about 30 to about 60 volume percent of the Herbal Extract Composition. When present, a Panax extract may comprise about 0.5 to 2 volume percent of the Modified Herbal Extract Composition, the remainder being Herbal Extract Composition. When present, a Crataegus extract may comprise about 0.5 to 2 volume percent, the remainder being Herbal Extract Composition. Sugar or artificial sweeteners can be added to foods or beverages prepared to contain the Modified Herbal Extract Composition.

As noted, the beverage of the invention comprises a Beverage Concentrate dissolved/dispersed in an aqueous carrier. The aqueous carrier may be distilled water, spring water, carbonated water, filtered water, and the like. The amount of the Modified Herbal Extract Composition contained in the beverage is dependent on a number of considerations. One consideration is taste and another is the desired physiological effect sought from ingestion of the beverage. The desired concentrations noted above is intended to be variable in recognition of these considerations.

The extraction processes used to isolate the desired extracts used in forming the Herbal Extract Composition and Modified Extract Composition of the invention utilizes traditional techniques in the art. The extraction is typically carried out at a temperature below that which adversely affects the properties of the extracted herbal composition or is above a reasonable reflux temperature for the extraction solvent of choice, and above that at which meaningful extraction does not occur. Generally, such temperatures range from as low as about 0° C. to 300° C., though temperatures that are higher or lower are feasible. Generally, the temperature of the extraction is dependent upon the boiling or freezing characteristic of the extraction solvent or solution. Moderate temperatures are preferred so long as extraction efficiencies for economic extraction rates are met. As a rule, higher temperatures are reflected in higher extraction rates.

The choice of extraction solvent is typically dependent upon the chemical nature of the herbal component undergoing extraction, the toxicity characteristics of the solvent, boiling and freezing points of the solvent, and the like considerations. Alcohols, such as ethanol, etc., are quite suitable as extraction solvents, neat or dissolved in water, and acetone, diethylether and aqueous ammonia are useful solvents in select cases. Ethanol is the preferred extraction solvent.

As a specific example of extraction for balm mint (*Melissa officinalis*), the starting material comprises 1 part dried leaves in 5-25 parts aqueous ethanol solution containing 60 weight % ethanol. The leaves are extracted with ethanol at 80°-95° C. and the organic residue is pressed and filtered when the temperature has reached ambient conditions. The extract has a shelf life of a least about 3 years.

As a specific example of extraction for oat (*Avena sativa*), the starting material comprises 1 part herb material in 1-5 parts ethanol (e.g. 100 g plant material per 100-500 g ethanol). For example, the plant is extracted with pure water and ethanol (95%) for 4-10 weeks and stirred on a daily basis. The organic residue is thereafter pressed and filtered. The extract has a shelf life of at least about 3 years.

As a specific example of extraction for linden (*Tilia europaea*), the starting material comprises 1 part dried flowers per 5-25 parts ethanol (e.g. 100 g flowers per 500-2500 g of 60% ethanol). When the mixture has reached ambient conditions, it is pressed and filtered. The extract has a shelf life of at least about 3 years.

In the case of Citrus species extract, they can be prepared by fermenting the juice and peel of a Citrus species and recovering the organic residue extract thereof. The optionally included Crataegus species extract is prepared by extracting the fruit and leaves in water and then in ethanol and recovering by filtration the organic residue extract thereof. Similarly, the optionally included Panax species extract is prepared by refluxing the dried root in a dilute aqueous ethanol and recovering by filtration the organic residue extract thereof. As well, the optionally included Lavendula species extract is prepared by extracting with heat the dried flowers in ethanol and recovering by filtration the organic residue extract thereof.

As a specific example of extraction for lemon (*Citrus medica*), the starting material comprises 1 part dried fruit in 2-10 parts water. The lemon juice is recovered and the peels are sliced. The juice and sliced peels are fermented at room temperature for 3-10 weeks and the organic residue is thereafter pressed and filtered. The clear extract is stored at 4° C.

As a specific example of extraction for Crateaegus (*Crataegus oxycanta*), the starting material comprises fruit and leaves (5:1 to 1:1 ratio w/w). The organic material is extracted in water (e.g. at 37° C.) for 0.5-3 hours. Thereafter, ethanol (95%) is added to reach a final ethanol concentration in the range of about 10–50%. The mixture is left for 4–12 weeks at 5°–30° C. After this period, the residue is pressed and filtered. The extract has a shelf life of at least about 3 years.

As a specific example for Panax (*Panax ginseng*), the starting material comprises 1 part dried ginseng root material per 2–20 parts ethanol. Organic material is refluxed for at least about 30 minutes in ethanol (10–50%). The residue is pressed and filtered when it has reached ambient temperature. The extract has a shelf life of at least about 3 years.

As a specific example for lavender (*Lavendula officinalis*), the starting material comprises 1 part dried lavender flower material per 10 parts ethanol. Flowers are extracted with 60% ethanol (80°–95° C.). The organic residue is pressed and filtered when the temperature has reached ambient. The extract has a shelf life of at least about 3 years.

One preferred embodiment provides a non-alcoholic beverage of particularly preferred extract proportions, e.g., a balm mint leaf extract, an oat plant extract and a linden flower extract. Preferably, the Melissa species extract comprises about 40 to 60 volume percent, the Avena species extract comprises about 20 to 30 volume percent and the remainder was Tilia species. An exemplary formulation of the beverage of the invention is Citrus extract (35.75 ml), *Melissa officinalis* extract (13.00 ml), *Avena sativa* extract (7.80 ml), *Tilia europaea* extract (3.25 ml), Panax ginseng extract (0.65 ml), *Crataegus oxyacanta* extract (0.65 ml) and *Lavendula officinalis* extract (0.07 ml), a total of 61.17 ml of extract, in 2,000 ml of natural spring water. Optionally, sugar can be included.

We claim:

1. A Herbal Extract Composition comprising a Melissa species extract, an Avena species extract and a Tilia species extract.

2. The Herbal Extract Composition of claim 1 wherein the Herbal Extract Composition comprises about 25 to about 75 volume percent of Melissa species extract, about 15 to about 50 volume percent of Avena species extract and about 3 to about 25 volume percent of a Tilia species extract.

3. The Herbal Extract Composition of claim 2 wherein the Herbal Extract Composition comprises about 30 to 65 volume percent of the Melissa species extract, about 20 to about 40 of the Avena species extract and about 5 to about 20 volume percent of the Tilia species extract.

4. A Modified Herbal Extract Composition comprising the Herbal Extract Composition of claim 1 and one or more of other extracts.

5. The Modified Herbal Extract Composition of claim 4 wherein the other extracts include one or more of Citrus, Crataegus, Panax and Lavendula species.

6. The Modified Herbal Extract Composition of claim 5 in the form of an extract concentrate that is useful in food and beverage preparations, as an additive or enhancer for solid and liquid foods and beverages.

7. The Modified Herbal Extract Composition of claim 6 in the form of a Beverage Concentrate composition.

8. The Modified Herbal Extract Composition of claim 7 wherein the Beverage Concentrate composition contains a lemon extract to enhance taste.

9. A beverage comprising the Beverage Concentrate Composition of claim 8 dispersed/dissolved in an aqueous carrier.

10. The beverage of claim 9 containing about 1 to about 50 volume percent of the Beverage Concentrate composition.

11. The beverage of claim 10 containing about 2 to about 45 volume percent of the Beverage Concentrate composition.

12. A beverage comprising the Beverage Concentrate Composition of claim 7 dispersed/dissolved in an aqueous carrier.

13. The beverage of claim 12 containing about 1 to about 50 volume percent of the Beverage Concentrate composition.

14. The beverage of claim 13 containing about 2 to about 45 volume percent of the Beverage Concentrate composition.

15. The beverage of claim 14 containing about 5 to about 40 volume percent of the Beverage Concentrate composition.

16. The beverage of claim 15 containing about 8 to about 35 volume percent of the Beverage Concentrate composition.

17. The beverage of claim 16 containing about 10 to about 30 volume percent of the Beverage Concentrate composition.

18. The Modified Herbal Extract Composition of claim 4 in the form of an extract concentrate that is useful in food and beverage preparations, as an additive or enhancer for solid and liquid foods and beverages.

19. The Modified Herbal Extract Composition of claim 18 in the form of a Beverage Concentrate composition.

20. The Modified Herbal Extract Composition of claim 19 wherein the Beverage Concentrate composition contains a lemon extract to enhance taste.

21. A beverage comprising the Beverage Concentrate Composition of claim 20 dispersed/dissolved in an aqueous carrier.

22. The beverage of claim 21 containing about 1 to about 50 volume percent of the Beverage Concentrate composition.

23. The beverage of claim 22 containing about 2 to about 45 volume percent of the Beverage Concentrate composition.

24. A beverage comprising the Beverage Concentrate Composition of claim 19 dispersed/dissolved in an aqueous carrier.

25. The beverage of claim 24 containing about 1 to about 50 volume percent of the Beverage Concentrate composition.

26. The beverage of claim 25 containing about 2 to about 45 volume percent of the Beverage Concentrate composition.

27. The beverage of claim 26 containing about 5 to about 40 volume percent of the Beverage Concentrate composition.

28. The beverage of claim 27 containing about 8 to about 35 volume percent of the Beverage Concentrate composition.

29. The beverage of claim 28 containing about 10 to about 30 volume percent of the Beverage Concentrate composition.

30. A process for preparing a Herbal Extract Composition which comprises:
    (a) extracting dried leaves of a Melissa species with heat in a non-toxic extraction solvent and recovering by filtration the organic residue extract thereof;

(b) extracting an Avena species in powder form in a non-toxic extraction solvent and recovering by filtration the organic residue extract thereof;

(c) extracting in a non-toxic extraction solvent the dried flowers of a Tilia species and recovering by filtration the organic residue extract thereof; and (d) combining the Melissa, Avena and Tilia extracts so recovered in the desired proportions to form the Herbal Extract Composition.

31. The process of claim 30 wherein the juice and peel of a Citrus species is fermented and the organic residue extract thereof is recovered and combined in the formation of a Modified Herbal Extract Composition.

32. The process of claim 30 wherein the fruit and leaves of a Crataegus species in water and then in ethanol is extracted, and recovering by filtration the organic residue extract thereof and thereafter combined in the formation of a Modified Herbal Extract Composition.

33. The process of claim 30 wherein dried root of a Panax species is extracted in a refluxing dilute aqueous ethanol solution and the organic residue extract thereof is recovered by filtration and combined in the formation of a Modified Herbal Extract Composition.

34. The process of claim 30 wherein the dried flowers of a Lavendula species are extracted with heated ethanol and the organic residue extract is recovered by filtration, and combined in the formation of a Modified Herbal Extract Composition.

* * * * *